United States Patent
Ghetler

(10) Patent No.: US 10,341,583 B2
(45) Date of Patent: Jul. 2, 2019

(54) FULL FIELD VISUAL-MID-INFRARED IMAGING SYSTEM

(71) Applicant: Agilent Technologies, Inc., Santa Clara, CA (US)

(72) Inventor: Andrew Ghetler, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/975,701

(22) Filed: May 9, 2018

(65) Prior Publication Data

US 2018/0262699 A1      Sep. 13, 2018

Related U.S. Application Data

(63) Continuation of application No. 14/743,854, filed on Jun. 18, 2015, now Pat. No. 10,003,754.

(51) Int. Cl.
*H04N 5/33* (2006.01)
*G01N 21/95* (2006.01)
(Continued)

(52) U.S. Cl.
CPC .............. *H04N 5/33* (2013.01); *G01N 21/35* (2013.01); *G01N 21/9501* (2013.01);
(Continued)

(58) Field of Classification Search
CPC .............. G01N 21/35; G01N 21/9501; G01N 21/9508; G02B 21/0064; G02B 21/367; H04N 5/23216; H04N 5/33
See application file for complete search history.

(56) References Cited

U.S. PATENT DOCUMENTS 8,289,503 B2    10/2012   Cohen et al.
2004/0232339 A1*  11/2004   Lanoue ............... G01N 21/255
                                                                              250/339.05
(Continued)

FOREIGN PATENT DOCUMENTS

WO    2009/050437 A1    4/2009
WO    2014/046606 A1    3/2014
(Continued)

OTHER PUBLICATIONS

European Search Report dated Nov. 28, 2016, Application No. 16173294.6.
(Continued)

*Primary Examiner* — Francis Geroleo

(57) ABSTRACT

An apparatus and method for generating images of specimens is disclosed. The apparatus includes an imaging system, controller, and user interface. The imaging system generates a plurality of component images of a specimen, each component image corresponding to a different viewing condition. Each image is represented by an intensity as a function of location on the specimen. The controller stores the component images and generates a compound image from a plurality of the component images. The compound image includes a weighted sum of first and second ones of the component images, the controller displaying the compound image on a display controlled by the controller. The user interface is adapted to control a weighting factor used in generating the weighted sum in response to user input. The controller redisplays the compound image after the weighting factor is changed in response to user input.

7 Claims, 6 Drawing Sheets

(51) Int. Cl.
*G02B 21/36* (2006.01)
*H04N 5/232* (2006.01)
*G01N 21/35* (2014.01)
*G02B 21/00* (2006.01)

(52) U.S. Cl.
CPC ..... *G01N 21/9508* (2013.01); *G02B 21/0064* (2013.01); *G02B 21/367* (2013.01); *H04N 5/23216* (2013.01)

(56) References Cited

U.S. PATENT DOCUMENTS

| | | |
|---|---|---|
| 2011/0129135 A1 | 6/2011 | Mizutani |
| 2012/0061590 A1 | 3/2012 | Khojasteh |
| 2013/0292571 A1 | 11/2013 | Mukherjee et al. |
| 2014/0028854 A1* | 1/2014 | Heinke .................. H04N 5/33 348/164 |

FOREIGN PATENT DOCUMENTS

| | | |
|---|---|---|
| WO | 2014/089499 A1 | 6/2014 |
| WO | 2014/190027 A1 | 11/2014 |

OTHER PUBLICATIONS

EP Office Action dated Dec. 21, 2017, Application No. 16173294.6.

* cited by examiner

FULL FIELD VISUAL-MID-INFRARED IMAGING SYSTEM

CROSS-REFERENCE TO RELATED PATENT APPLICATIONS

This application is a continuation of U.S. patent application Ser. No. 14/743,854 filed on Jun. 18, 2015, now U.S. Pat. No. 10,003,754, said patent application being incorporated by reference herein.

BACKGROUND

Quantum cascade lasers provide a tunable mid-infrared (MIR) light source that can be used for spectroscopic measurements and images. Many chemical components of interest have molecular vibrations that are excited in the MIR region of the optical spectrum, which spans wavelengths between 5 to 25 microns. Hence, measuring the absorption of MIR light at various locations on a sample can provide useful information about the chemistry of the sample as a function of position on the sample.

SUMMARY

The present invention includes an apparatus and method for generating images of specimens. The apparatus includes an imaging system, controller, and user interface. The imaging system generates a plurality of component images of a specimen, each component image corresponding to a different viewing condition. Each image is represented by an intensity as a function of locations on the specimen. The controller stores the component images and generates a compound image from a plurality of the component images. The compound image includes a weighted sum of first and second ones of the component images, the controller displaying the compound image on a display controlled by the controller. The user interface is adapted to control a weighting factor used in generating the weighted sum in response to user input. The controller redisplays the compound image after the weighting factor is changed in response to user input.

In one aspect of the invention, one of the component images is stored in compressed format by the controller.

In another aspect of invention, the first component image includes a region having a different spatial resolution than the second component image.

In another aspect of invention, the first component image corresponds to the specimen being illuminated by a different wavelength of light than the second component image. The first component image can include intensity values for the entire specimen.

In another aspect of invention, the second component image does not have intensity values for points on the specimen at which the first component image has intensity values.

In another aspect of invention, the second component image includes regions having different spatial resolutions.

In another aspect of invention, the controller is adapted to receive information specifying a viewing condition and a scan region on the specimen, the controller causing the imaging system to generate an image of the specimen using the viewing condition in the scan region. The viewing condition can include an illumination wavelength, and if no other component image has a viewing condition with that illumination wavelength, the controller defines a new component image for the generated image. The scan region can include a region of an existing component image, and the generated imaging replaces intensity values at corresponding locations in the existing component image.

In another aspect of invention, each image is represented by a vector-valued function as a function of locations on the specimen, the intensity as a function of location on the specimen being one component of that vector-valued function. The controller can convert the compound image to a colored image, the color components depending on the vector-valued components.

DETAILED DESCRIPTION

Figure 1:
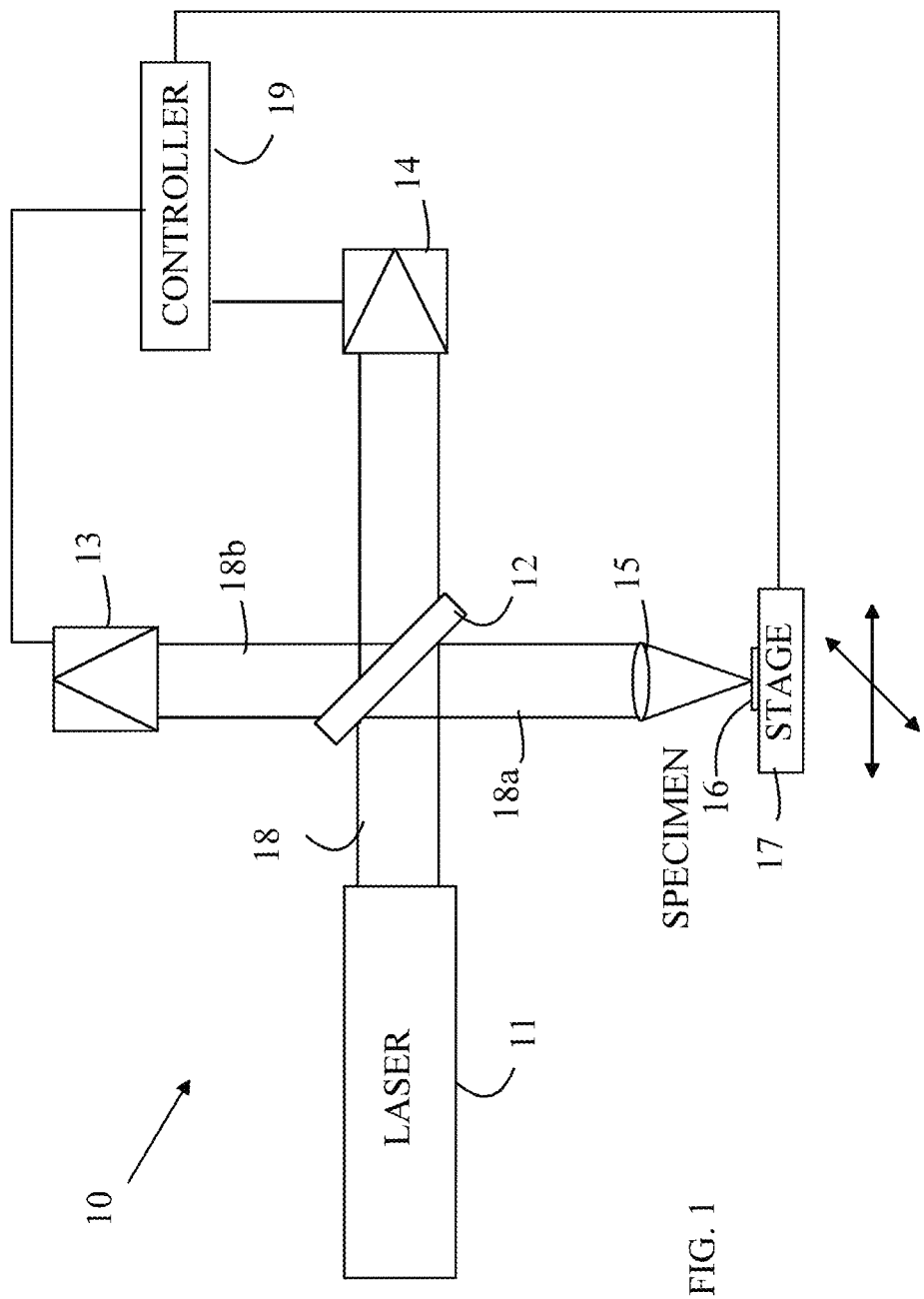
FIG. 1 illustrates one embodiment of a scanning MIR imaging system.

The manner in which the present invention provides its advantages can be more easily understood in the context of a scanning MIR imaging system that also provides an image in the visual spectrum of the specimen being scanned. Refer now to FIG. 1 which illustrates one embodiment of a scanning MIR imaging system. Imaging system 10 includes a quantum cascade laser 11 that generates a collimated light beam 18 having a narrow band of wavelengths in the MIR. In one aspect of the invention, quantum cascade laser 11 is a quantum cascade laser having a tunable wavelength that is under the control of a controller 19. Collimated light beam 18 is split into two beams by a partially reflecting mirror 12. Light beam 18a is directed to a lens 15 that focuses that beam onto a specimen 16 that is mounted on xy-stage 17 that can position specimen 16 relative to the focal point of lens 15. Light that is reflected back from specimen 16 is collimated into a second beam that has a diameter determined by the aperture of lens 15 and returns to partially reflecting mirror 12 along the same path as light beam 18a. While the first and second beams are shown as having the same cross-section in FIG. 1, it is to be understood that the second beam could have a different cross-section than the first beam. A portion of the second beam is transmitted through partially reflecting mirror 12 and impinges on a first light detector 13 as shown at 18b. Light detector 13 generates a signal related to the intensity of light in beam 18b. Controller 19 computes an image as a function of position on specimen 16 by moving specimen 16 relative to the focal point of lens 15 using xy-stage 17.

Controller 19 also monitors the beam intensity of the light in collimated light beam 18 using a second light detector 14 that receives a portion of the light generated by quantum cascade laser 11 through partially reflecting mirror 12. Quantum cascade laser 11 is typically a pulsed source. The intensity of light from pulse to pulse can vary significantly, and hence, the pixels of the image are corrected for the variation in intensity by dividing the intensity measured by light detector 13 by the intensity measured by light detector 14. In addition, since the light intensity from quantum cascade laser 11 is zero between pulses, controller 19 only sums the ratio of intensities from light detectors 13 and 14 during those times at which the output of light detector 14 is greater than some predetermined threshold. This aspect of the present invention improves the signal-to-noise ratio of the resultant image, since measurements between pulses contribute only noise, which is removed by not using measurements between pulses.

The potential resolution in terms of scan lines of this type of imaging system is very large. The maximum specimen size is set by the maximum travel of the specimen stage. Stages that move tens of centimeters are easily accommodated. The spot size on the specimen is limited by optics to one or two wavelengths of the MIR light. Hence, a spot size of 30 microns is achievable. Thus, to scan a large specimen at the highest resolution requires thousands of scan lines. Accordingly, reducing the scanning time is of utmost importance.

Figure 2:
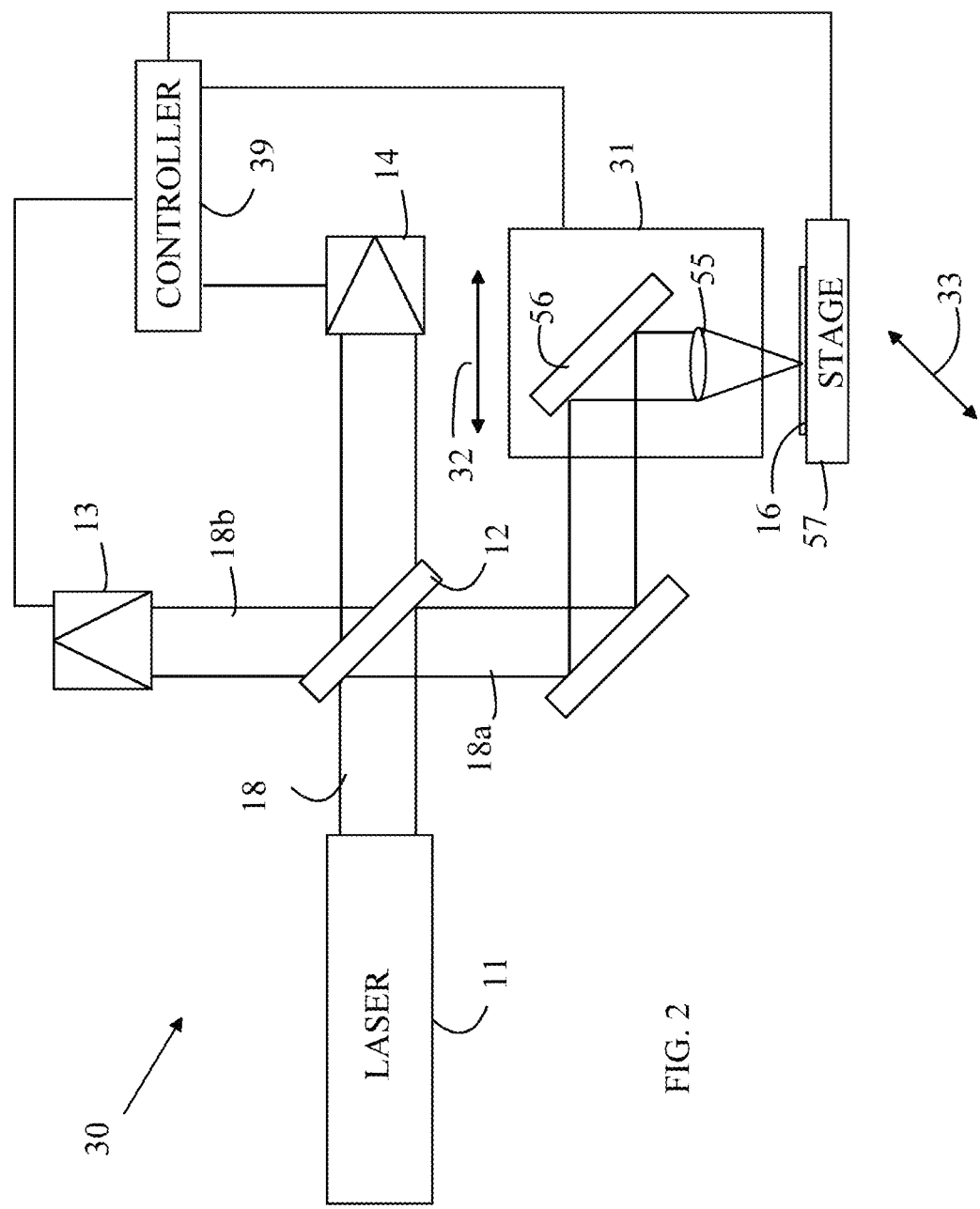
FIG. 2 illustrates an embodiment of an imaging system in which the lens assembly moves.

In the above described embodiments, the stage moves the sample in two dimensions. However, the stage has a significant mass, and hence, the speed at which the sample is imaged is limited by the motion of the stage. In embodiments in which rapid imaging time is important, embodiments in which the specimen is scanned in one direction by moving lens 15 are preferred. Refer now to FIG. 2, which illustrates an embodiment of an imaging system in which the lens assembly moves. In imaging system 30, the stage assembly is divided into two components. Component 31 includes focusing lens 55 and is moveable in a direction shown at 32 such that a single line of the image is generated with each pass of component 31. Since focusing lens 55 and mirror 56 have a mass that is small compared to component 57, component 31 can be moved with much greater speed. In one embodiment, component 31 is mounted on a rail and moved in a manner analogous to a print head on an inkjet printer. The second component of the stage assembly is shown at 57. Component 57 includes the mounting mechanism for the specimen being scanned and moves in a direction 33 that is orthogonal to direction 32. Since component 57 only needs to move once per scan line, the slower speed of motion associated with the more massive component 57 is acceptable. Controller 39 provides control functions analogous to controller 19 shown in FIG. 19.

However, even with this improved scanning speed, a complete scan of a large specimen could require hours, particularly, if scanning at a number of different MIR wavelengths is required. Accordingly, an arrangement in which the specimen can be imaged in the visible wavelengths followed by the user selecting specific areas to be scanned in the MIR would be advantageous.

Figure 3:
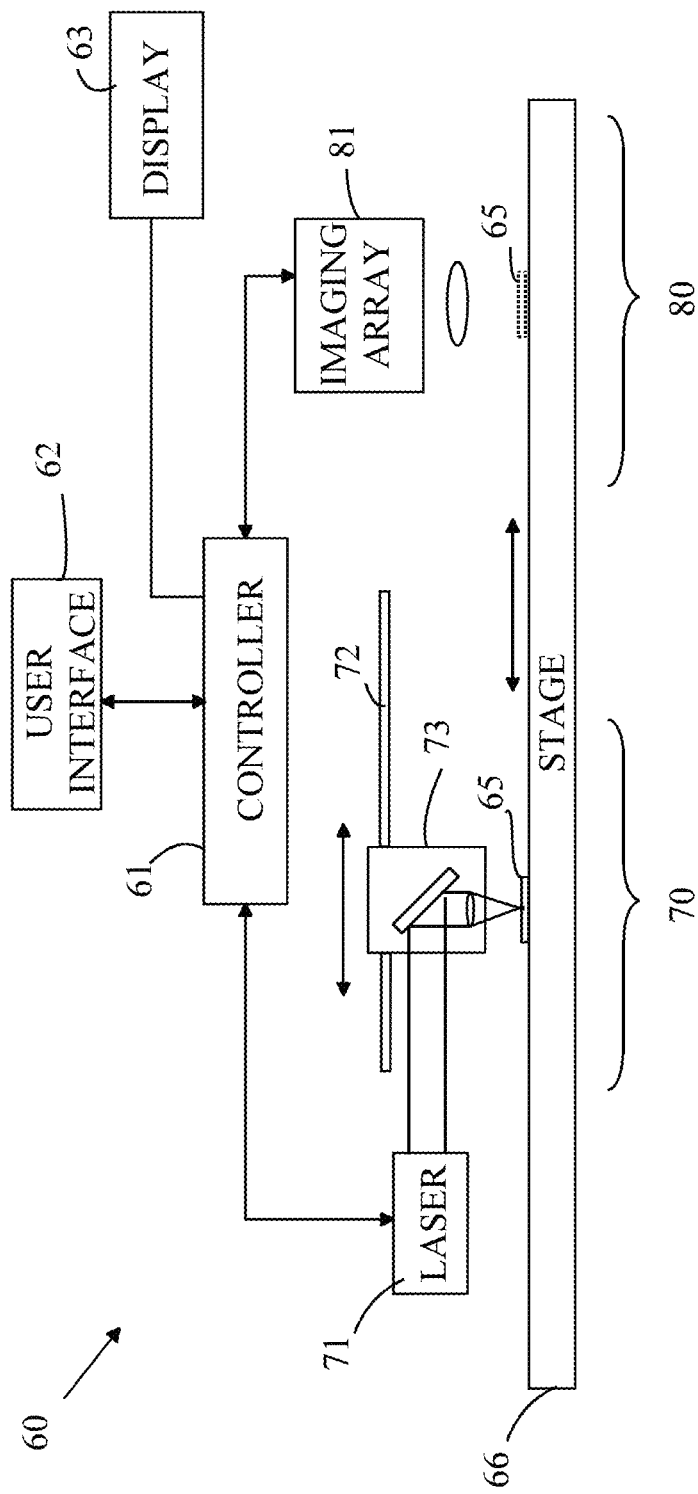
FIG. 3 illustrates an embodiment of a MIR imaging system that combines a visual imaging system with a MIR imaging system.

Refer now to FIG. 3, which illustrates an embodiment of a MIR imaging system that combines a visual imaging system with a MIR imaging system. Imaging system 60 includes a MIR imaging system 70 and a visible light imaging system 80 having an imaging array 81 that is responsive to light in the visible wavelengths. Both systems are under the control of controller 61. The two imaging systems share a stage 66 that allows a specimen 65 to be moved between the imaging systems such that an area defined using visible light imaging system 80 can be positioned for scanning using MIR imaging system 70. MIR imaging system 70 includes a scanning head 73 that moves on a rail 72 under the control of controller 61 in a manner analogous to that described above with respect to imaging system 30 shown in FIG. 3. Stage 66 allows the specimen to be moved in a direction perpendicular to the direction of travel of scanning head 73 so that a two-dimensional image can be generated. To simplify the drawing, the laser and associated optics in MIR imaging system 70 are shown as a single block 71.

In practice, a user places specimen 65 in position under visible light imaging system 80 and indicates which portion of specimen 65 is to be scanned using a user interface 62 and display 63. The user can indicate the desired area using a point device or similar apparatus. The visible image is generated using an objective lens that provides the desired level of magnification. Controller 61 then computes the distance specimen 65 must be moved to be properly aligned with MIR imaging system 70. Specimen 65 is then moved and scanned as described above.

Managing and viewing the large amount of data generated in these multiple scans presents significant challenges. In general, there will be one visible image of the entire specimen and a number of small area scans at various locations on the specimen. In addition, some areas of interest can have multiple scans at different wavelengths. Finally, different sub-images can have different spatial resolutions.

Figure 4:
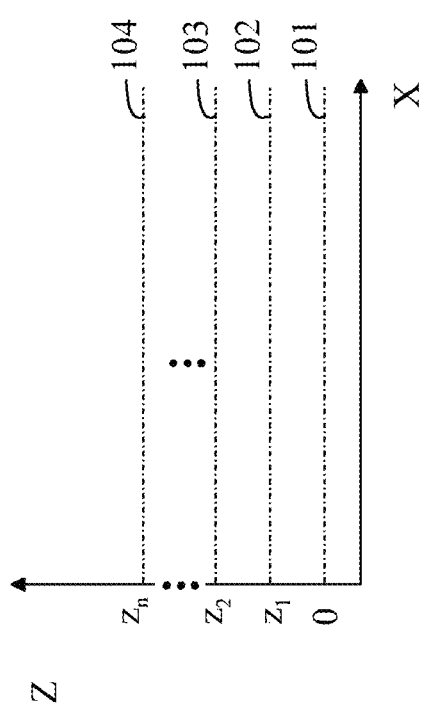
FIG. 4 illustrates a cross-section through a y-plane in the three-dimensional image.

The present invention utilizes a three-dimensional image structure to manage this large amount of information. For the purposes of the present discussion, any given image is defined as an intensity function on an x-y plane. For example, an image in the visual wavelength could be represented by an intensity of reflected light as a function of the stage position (x,y) of the point being measured. In the z-direction, the image is divided into "layers". Refer now to FIG. 4, which is a cross-section through a y-plane in the three-dimensional image. Each layer is an image associated with a particular wavelength of MIR light or visible light. Exemplary planes are shown at 101-104. To simplify the following discussion, it will be assumed that the visual image is a monochrome image located at z=0, i.e., plane 101. However, the visual image could be a "color" image, in which case, the image pixels would be vectors defined on the x-y plane corresponding to the visual image. To simplify the present discussion, it will be assumed that all images are scalar valued intensities as a function of (x,y). The extension of the invention to a vector-valued image pixel will be discussed in more detail below.

In general, the (x,y) coordinates are not continuous values, but rather digital values that represent locations on the sample stage. The finest increments in x,y are preferably set to be the spacing of the highest resolution measurements in x,y. That is, the stage is moved by a distance of 1 unit in x or y between successive measurements. In general, the resolution at which any given image or portion of an image is taken can vary from region to region in the image or change with wavelength. For example, in one region of interest on the sample, a region could be scanned with the smallest possible spot size and incrementing the stage by a distance of one count in x or y. In another region, samples could be taken by incrementing the stage by two counts between measurements to improve the speed of the measurements.

When displaying an image, the resolution with which the data was taken is reflected in the pixel size on the image. There is a one-to-one relationship between the pixels and the coordinates on the sample stage. At the highest resolution, each pixel represents a 1×1 square on the sample stage and the intensity of that pixel is determined by the measured reflectivity of the corresponding point on the sample. If measurements are only taken every two pixels, then each measurement represents an estimate of the intensity at the four pixels that include the measurement point. The intensities of these four pixels are set to the measured value.

Figure 5:
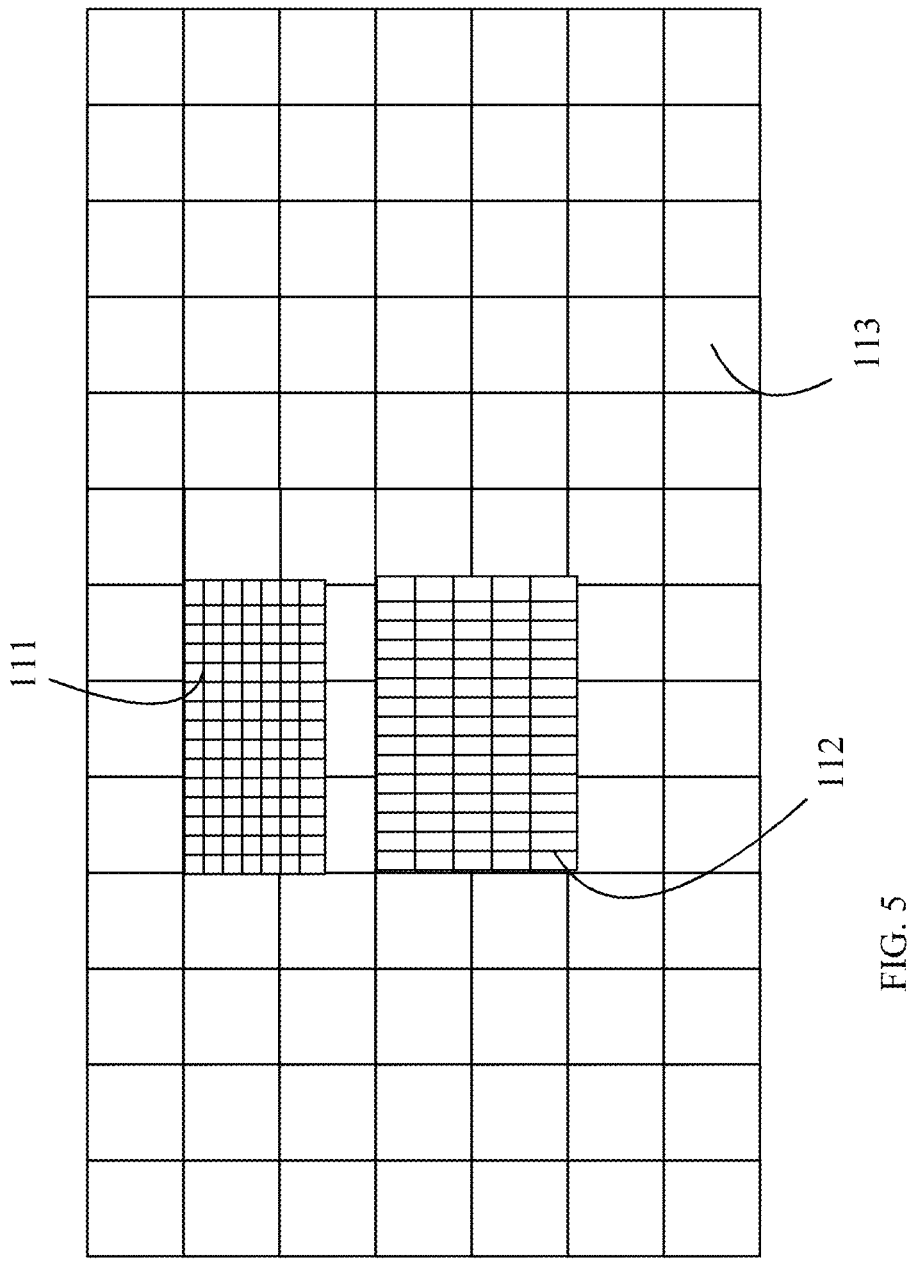
FIG. 5 illustrates a multi-resolution image according to one embodiment of the present invention.

Refer now to FIG. 5, which illustrates a multi-resolution image according to one embodiment of the present invention. In this example, most of the specimen is scanned by taking points every five counts in the sample stage position. Hence, these pixels are 5×5 squares such as pixel 113. A small portion of the image was scanned at the resolution of one measurement for each count in the sample stage position. These pixels are shown at 111, and consist of 1×1 squares.

It should be noted that in embodiments that utilize a fast moving lens assembly for scanning in the x direction, no time improvement is obtained by taking data at coarser intervals in the x-direction. The increased speed is obtained by incrementing the stage position in the y-direction by multiple counts between scans. For example, the stage could be incremented by two counts in the y-direction between x scans that take data every count in the x-direction. In this case, the pixels are represented by 1×2 rectangles that have an intensity determined by the values measured at x position. A region with such pixels is shown at 112.

In general, the visible image will be recorded over the entire sample stage. The other images, however, may only be recorded over smaller areas. In addition, those smaller areas may differ from image to image. Hence, keeping track of the locations of the portions of the other images that have been measured presents challenges. In one aspect of the invention, the controller provides an image display in which multiple images are viewed superimposed on one another with the upper images being partially transparent. In essence, the user views the image stack from a position above the stack on the z-axis with the individual images assigned a transparency value, so that features in the lower images can be seen through the upper images. In the simplest case, only two images are visible at once, i.e., the other images are assigned a transparency that renders those images invisible.

Figure 6:
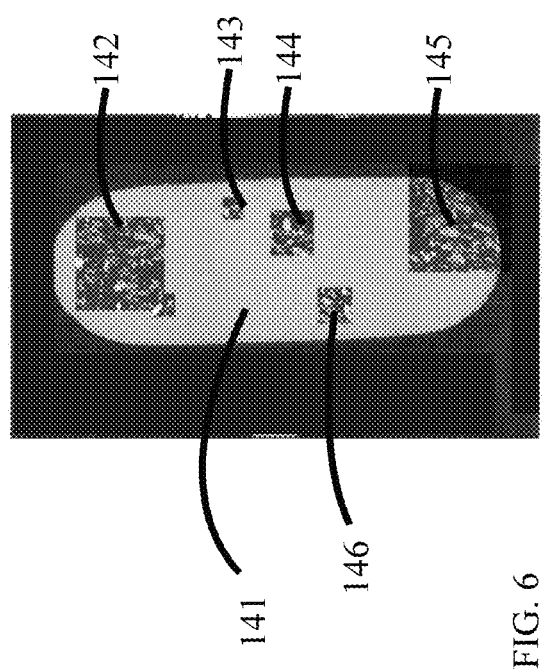
FIG. 6 illustrates a display in which the visible image and one of the MIR images are chosen for display.

Refer now to FIG. 6, which illustrates a display in which the visible image and one of the MIR images are chosen for display. In this example, the sample consists of a capsule such as an aspirin tablet. The distribution of the aspirin in the tablet can be viewed in the MIR, since the aspirin absorbs in the MIR and the filler material does not. The visual image is shown at 141. A number of MIR images of portions of the specimen are shown at 142-146. The regions of the MIR image that have not been scanned are completely transparent. While the MIR scanned areas in this example are sufficiently opaque to block the underlying visual image, it is to be understood that the transparency of the regions shown at 142-146 could be set to allow the underlying visual image to be viewed through the MIR imaged regions.

In one aspect of the invention, the transparency of the upper image can be continuously set with a control such as a slider. The user can start with the slider set such that the upper image is completely transparent, and hence, the user is viewing only the underlying visible image. As the user increases the opaqueness of the upper layer, the upper layer becomes visible and the user can compare features in the two images. As the user further increases the opaqueness of the upper layer, the underlying image becomes blocked by the regions of the upper image that have been scanned.

In the above example, the bottom layer was the visible image; however, the user can define any two images as the upper and lower layers for viewing. Hence, the user can view portions of the sample at two different MIR scan wavelengths and pan from one to the other to view the changes in the images with wavelength.

In one aspect of the invention, the individual images are assigned distinct colors. Hence, the areas in which the images overlap will be seen in a distinct color that depends on the transparency and colors chosen for the individual images. For example, red could be assigned for the first layer and blue for the second layer. Features that are present in both images would then be seen in various shades of purple.

The above described examples utilize two layers for viewing. However, embodiments in which the user defines a transparency level and color for each layer in the stack of images can also be constructed.

A display according to the present invention can be used to direct the imaging system during scanning. The user can view one of the images and choose a region to be scanned. The user then enters the scanning parameters such as the resolution and wavelength of light to be used. The imaging system then scans that region and enters the new data into the array that stores the three-dimensional image. If the wavelength chosen matches a wavelength for which an image plane has already been defined, the new data is entered on that plane. If other imaging data is already present on that plane at the corresponding x,y values, the new data replaces the existing data and is entered at the new resolution. For example, the user could choose a region in which a coarse resolution scan had already been made to provide data at a finer resolution. The new fine resolution data would then be entered to replace the previously scanned data.

The display system of the present invention can be applied to a number of different imaging systems in addition to those described above. For example, one type of system for generating images in the MIR can be viewed as a conventional microscope with a MIR light source and an optical system that images the illuminated sample onto an array of MIR detectors. A MIR light source based on a quantum cascade laser provides a tunable MIR light source. There are several problems with such imaging systems. In such systems, a high resolution image of a large specimen must be generated by "stitching" together a number of smaller high resolution images. The specimen can be scanned at a low resolution to achieve an image of an entire large specimen. The magnification is then changed and smaller high resolution images are taken. These images may be combined to provide a high resolution image of the specimen or may remain as isolated high resolution areas. In addition, the specimen or parts thereof, can be scanned at different wavelengths to provide additional images. Hence, a display problem that is analogous to that described above is also encountered in this type of imaging system.

Accordingly, the display system of the present invention is applicable to any scanning system in which a number of images of the same specimen are generated under different "viewing conditions" without altering the specimen. A viewing condition is defined to be the illumination conditions of the specimen such as wavelength and intensity of incident light and the measurement conditions for the light absorbed or reflected by the specimen. In one set of viewing conditions, the illumination wavelength differs from image to image. In a second set of viewing conditions, two or more images are taken with the same incident light wavelength, but the light leaving the specimen is viewed through different forms of filters. For example, the illuminating light could be linearly polarized in a first direction and a polarization filter used to view the light leaving the specimen. Such systems are useful in separating light that is diffusely reflected from the specimen from light that is specularly reflected from the specimen. In one aspect of the invention, the specimen is not removed from the scanning apparatus between images.

In this general case, each image is stored on a different image plane in a manner analogous to that discussed above. Each image will be referred to as a component image in the following discussion. The component images are registered with respect to one another. That is, the (x,y) coordinates of the intensity values in each component image are all referenced to the (x,y) coordinates of the specimen. This allows a plurality of component images having different viewing conditions to be compared by overlapping the images at different transparencies and/or panning from one image to another. For the purposes of the present discussion, a viewing condition is defined to be the illumination wavelength of the specimen, the resolution of the image generated, the sample points on the specimen at which the image intensity is actually measured, and any filters or transformations used to process the data collected at those sample points to generate an intensity as a function of position on the specimen.

The individual component images can have regions of different spatial resolution within the component image as discussed above. In addition, the individual component images can be incomplete in that only part of the specimen was scanned to generate that image. It is advantageous to have one component image that is a complete image of the specimen under one viewing condition to provide a reference that allows the other component images to be placed in geometric context with each other. In the above examples, that reference image was a component image generated by using light in the visible range of wavelengths. However, other viewing conditions could be utilized for the reference image.

The controller generates a compound image by forming a weighted sum of two or more component images. The weight factors used to combine the component images are equivalent to the transparency factor discussed above. A small weighting factor renders the corresponding component image more transparent than a larger weighting factor. The compound image $C(x,y)$ for two component images, $I_1(x,y)$ and $I_2(x,y)$ is given by $C(x,y)=w_1 I_1(x,y)+w_2 I_2(x,y)$, where $w_1$ and $w_2$ are the weight factors. The sum of the weight factors is preferably one to prevent changes in overall intensity of the compound image as the weight factors are changed.

To combine two component images, there must be corresponding intensity values in each component image. As noted above, a component image can include pixels of different sizes. For example, if an intensity is only measured at every fifth point on the specimen, there will not be intensity values at the other points. The present invention fills in the missing points by replicating the measured values at each of the missing points.

In addition, the component image may only include data in a limited region of the specimen area. In one aspect of the invention, when an image plane is defined, the component image is initialized to intensity values of zero. Each component image is defined to have storage locations for each possible (x,y) coordinate on the specimen. As data is generated for various regions in that component image, the new data values replace the corresponding zeros. The regions that are not measured remain zero, and hence, appear completely transparent when the compound image is generated.

To save memory, the image plane may be stored in a compressed format rather than providing a two dimensional array of pixels in memory. For example, if only a small fraction of the image plane is non-zero, schemes in which the coordinates of each of the small non-zero pixels are stored together with the intensity values corresponding to those pixels can be utilized. If the image plane has rectangular islands of measured pixels, the coordinate of a reference point in each island can be stored together with the small measured image. When a pixel value is required, the compressed image can be decompressed to provide the desired pixel value. If the coordinate of the pixel is not in one of the non-zero regions, or "islands", a value of zero is returned. Schemes that detect long runs of a particular pixel value such as a zero can also be used to compress the image plane data in sparsely populated image planes.

The above-described embodiments have utilized images comprising an intensity as a function of location on the specimen. However, an image can be defined as a set of vector values defined as a function of position on the specimen. For example, in an image in the visual wavelengths, each point on the specimen could be characterized by a color vector having a plurality of components, each component representing an intensity at a different color.

The controller can likewise generate a compound image in which each (x,y) value on the specimen has a vector associated with that location. In this case, the vector is a plurality of intensity values. The weighting process is performed on each component of the vector to provide a weighted vector-valued image. In the case of a three component vector, the image can be displayed as a colored image. As noted above, individual component images can be assigned colors. Hence, an intensity based image can be converted to a vector-valued image by multiplying each component of a unit color vector by the measured intensity. This allows the controller to provide a colored component image.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:
1. A scanning system comprising:
  a first scanning station that generates component images of a specimen at visual wavelengths;
  a second scanning station that generates component images of portions of said specimen at wavelengths that are different from wavelengths used by said first scanning station;
  a stage that moves specimen between first and second scanning stations to allow specimen to be scanned at each scanning station without being removed from said scanning system;
  a controller that stores said component images, generates a compound image from a plurality of said component images, said compound image comprising a weighted sum of first and second ones of said component images, said controller displaying said compound image on a display controlled by said controller; and
  a user interface adapted to control a weighting factor used in generating said weighted sum in response to user input, said controller redisplaying said compound image after said weighting factor is changed in response to user input;

wherein one of said component images has a first region with spatial resolution that is different from a spatial resolution in a second region of that component image.

2. The system of claim 1 wherein said second scanning station generates images using a mid-infrared (MIR) light source.

3. The system of claim 1 wherein said plurality of component images includes a third component image generated by said second scanning station for a region of said specimen identified by user supplied information from a fourth component image generated by said second scanning station.

4. The system of claim 1 wherein said controller is adapted to receive information specifying a viewing condition and a scan region on said specimen, said controller causing said second scanning station to generate an image of said specimen using said viewing condition in said scan region.

5. The system of claim 4 wherein said viewing condition comprises a viewing condition wavelength and no other component image has a viewing condition with that illumination wavelength, said controller defining a new component image for said generated image.

6. The system of claim 4 wherein said scan region comprises a region of an existing component image, said generated imaging replacing intensity values at corresponding locations in said existing component image.

7. The system of claim 1 wherein a plurality of said component images comprises scalar valued functions generated under different viewing conditions and a compound image generated from said plurality of component images comprises a vector valued function.

* * * * *